United States Patent
Graham et al.

(10) Patent No.: US 10,413,178 B2
(45) Date of Patent: Sep. 17, 2019

(54) FLEXIBLE GONIOSCOPIC LENS

(71) Applicant: Ocular Instruments, Inc., Bellevue, WA (US)

(72) Inventors: Raymond D. Graham, Renton, WA (US); Andrew Schieber, Aliso Viejo, CA (US)

(73) Assignee: Ocular Instruments, Inc., Bellevue, WA (US)

( * ) Notice: Subject to any disclaimer, the term of this patent is extended or adjusted under 35 U.S.C. 154(b) by 0 days.

(21) Appl. No.: 15/457,745

(22) Filed: Mar. 13, 2017

(65) Prior Publication Data

US 2017/0181622 A1 Jun. 29, 2017

Related U.S. Application Data

(62) Division of application No. 14/712,100, filed on May 14, 2015, now abandoned.

(60) Provisional application No. 61/996,827, filed on May 14, 2014.

(51) Int. Cl.
   *A61B 3/117* (2006.01)
   *A61B 3/125* (2006.01)
   *G02C 7/04* (2006.01)
   *A61B 3/00* (2006.01)

(52) U.S. Cl.
   CPC ............ *A61B 3/117* (2013.01); *A61B 3/0091* (2013.01); *A61B 3/125* (2013.01); *G02C 7/047* (2013.01); *G02C 7/048* (2013.01); *G02C 7/049* (2013.01)

(58) Field of Classification Search
   CPC ....... A61B 3/117; A61B 3/1173; A61B 3/125; G02C 7/047; G02C 7/048; G02C 7/049
   USPC ..... 351/159.04, 159.17, 159.18, 159.23, 219
   See application file for complete search history.

(56) References Cited

U.S. PATENT DOCUMENTS

| | | | |
|---|---|---|---|
| 5,009,497 A | 4/1991 | Cohen | |
| 5,347,326 A * | 9/1994 | Volk | A61B 3/125 351/159.02 |
| 5,617,154 A * | 4/1997 | Hoffman | B29D 11/00317 351/159.32 |
| 5,953,097 A | 9/1999 | Stark | |

(Continued)

FOREIGN PATENT DOCUMENTS

JP 2007-151739 A 6/2007
WO 2012/061160 A1 5/2012

OTHER PUBLICATIONS

Extended European Search Report dated Oct. 6, 2015, issued in corresponding European Application No. 15167730.9, filed May 14, 2015, 8 pages.

*Primary Examiner* — Jordan M Schwartz
(74) *Attorney, Agent, or Firm* — Christensen O'Connor Johnson Kindness PLLC

(57) ABSTRACT

A self-adhering, flexible gonioscopic lens for adhering to cornea and scleral regions of an eye includes a central lens having a body including a contact surface and a viewing surface, the contact surface having a radius of curvature that approximates the radius of curvature of the cornea, an eye fixation system configured for fixing the central lens to the eye, wherein the eye fixation system is attached to the annular perimeter of the contact surface of the central lens, extending around only a portion of the annular perimeter of the contact surface of the central lens to define a cut-out portion in the eye fixation system of the gonioscopic lens.

9 Claims, 13 Drawing Sheets

(56) References Cited

U.S. PATENT DOCUMENTS

| | | | |
|---|---|---|---|
| 5,963,301 A * | 10/1999 | Volk | A61F 9/013 |
| | | | 351/219 |
| 6,120,147 A | 9/2000 | Vijfvinkel et al. | |
| 6,161,931 A | 12/2000 | Slishman | |
| 6,412,946 B1 | 7/2002 | Vijfvinkel et al. | |
| 6,926,406 B2 | 8/2005 | Mitsui | |
| 2006/0050229 A1 * | 3/2006 | Farberov | A61B 3/117 |
| | | | 351/159.02 |
| 2006/0152673 A1 | 7/2006 | Cotie et al. | |
| 2007/0273825 A1 | 11/2007 | Legerton et al. | |
| 2009/0303434 A1 | 12/2009 | Tung | |
| 2010/0134759 A1 * | 6/2010 | Silvestrini | A61B 3/117 |
| | | | 351/206 |
| 2010/0265461 A1 * | 10/2010 | Gille | A61B 3/117 |
| | | | 351/219 |
| 2012/0057121 A1 | 3/2012 | Dewoolfson et al. | |
| 2012/0099077 A1 | 4/2012 | Abt | |
| 2012/0257167 A1 | 10/2012 | Gille et al. | |
| 2013/0103014 A1 * | 4/2013 | Gooding | A61B 3/102 |
| | | | 606/6 |
| 2013/0293832 A1 * | 11/2013 | de Juan, Jr. | G02C 7/04 |
| | | | 351/159.33 |

* cited by examiner

FLEXIBLE GONIOSCOPIC LENS

CROSS-REFERENCE TO RELATED APPLICATION

This application is a divisional of U.S. patent application Ser. No. 14/712,100, filed May 14, 2015, which claims the benefit of U.S. Provisional Application No. 61/996,827, filed May 14, 2014, the disclosures of which are hereby incorporated by reference herein in their entirety.

SUMMARY

The present disclosure relates generally to instruments of the type broadly applicable to ophthalmology procedures. As will be described in more detail below, the one or more examples of instruments include a gonioscopic lens configured for direct contact and adherence to parts of an eye.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with one embodiment of the present disclosure, a self-adhering, flexible, contact gonioscopic lens for adhering to cornea and scleral regions of an eye is provided. The gonioscopic lens includes (a) a central lens having a body including a contact surface and a viewing surface, the contact surface having a radius of curvature that approximates the radius of curvature of the cornea; and (b) an eye fixation system configured for fixing the central lens to the eye, wherein the eye fixation system is attached to the perimeter of the contact surface of the central lens, extending around only a portion of the perimeter of the contact surface of the central lens to define a cut-out portion in the eye fixation system of the gonioscopic lens.

In accordance with another embodiment of the present disclosure, a method of performing a surgical procedure on an eye having a cornea and a sclera, is provided. The method includes placing a lens on the eye, the lens having a central lens including a contact surface and a viewing surface, the contact surface having a radius of curvature R1 that approximates the radius of curvature of the cornea, and an eye fixation system attached to the central lens having a radius of curvature R2 that is less than R1 and less than the radius of curvature of the sclera; and moving the lens to a first position to view a first area of the anterior chamber of the eye through the viewing surface.

In accordance with another embodiment of the present disclosure, a method of performing a surgical procedure on an eye having a cornea and a sclera is provided. The method includes placing a lens on the eye, the lens having a central lens including a contact surface and a viewing surface, the contact surface having a radius of curvature R1 that approximates the radius of curvature of the cornea, and an eye fixation system attached to the central lens; moving the lens to a first position to view a first area of the anterior chamber of the eye through the viewing surface; and moving the lens to a second position on the eye to view a second area of the anterior chamber of the eye through the viewing surface.

In accordance with another embodiment of the present disclosure, a self-adhering, flexible contact lens for adhering to cornea and scleral regions of an eye is provided. The cornea and sclera each have a radius of curvature with the radius of curvature of the sclera being greater than the radius of curvature of the cornea. The contact lens includes: (a) a central lens having a body including a contact surface and a viewing surface, the contact surface having a radius of curvature that approximates the radius of curvature of the cornea; and (b) an eye fixation system attached to the central lens, the eye fixation system including a plurality of protrusions extending from or near at least a portion of the perimeter of the central lens, each protrusion configured to interface with the sclera, and each protrusion having a first end and a second end, the first end being attached to the central lens.

In accordance with another embodiment of the present disclosure, a self-adhering, flexible contact lens for adhering to cornea and scleral regions of an eye is provided. The cornea and sclera each having a radius of curvature with the radius of curvature of the sclera being greater than the radius of curvature of the cornea. The contact lens includes: (a) a central lens having a body including a contact surface and a viewing surface, the contact surface having a radius of curvature R1 that approximates the radius of curvature of the cornea; (b) an eye fixation system attached to the central lens; and (c) a cut-out portion of the contact lens.

In any of the embodiments or methods described herein, the contact lens may be molded as a single piece.

In any of the embodiments or methods described herein, the contact lens may be made from silicone.

In any of the embodiments or methods described herein, the eye fixation system may be continuous as it extends around the perimeter of the contact surface of the central lens.

In any of the embodiments or methods described herein, the eye fixation system may be non-continuous as it extends around the perimeter of the contact surface of the central lens.

In any of the embodiments or methods described herein, the eye fixation system may include a flange portion.

In any of the embodiments or methods described herein, the contact lens may have a cut-out portion.

In any of the embodiments or methods described herein, the cut-out portion may be shaped such that at least one surgical tool can access to the cornea without moving the contact lens.

In any of the embodiments or methods described herein, the viewing surface may be flat.

In any of the embodiments or methods described herein, the viewing surface may be prismatic.

In any of the embodiments or methods described herein, the viewing surface may be rounded.

In any of the embodiments or methods described herein, the central lens may include at least one hole extending from the viewing surface into the body of the central lens, the at least one hole adapted to accept a surgical tool for manipulation of the contact lens.

In any of the embodiments or methods described herein, the at least one hole may be a blind hole.

In any of the embodiments or methods described herein, the contact lens may be configured for movement on the eye of the patient.

In any of the embodiments or methods described herein, a method of use further includes moving the lens to a second position on the eye to view a second area of the anterior chamber of the eye through the viewing surface.

In any of the embodiments or methods described herein, the protrusions may extend around the entire perimeter of the contact surface of the central lens.

In any of the embodiments or methods described herein, the protrusions may extend around at least a portion of the perimeter of the contact surface of the central lens.

In any of the embodiments or methods described herein, the eye fixation system may include a flange, wherein the protrusions are attached to the flange.

In any of the embodiments or methods described herein, the second end of each of the plurality of protrusions may be flat.

In any of the embodiments or methods described herein, the second end of each of the plurality of protrusions may be rounded.

In any of the embodiments or methods described herein, the eye fixation system may include a flange, at least a portion of the flange having a radius of curvature R2 less than the radius of curvature of the sclera and greater than R1, less than R1 or equal to R1.

DESCRIPTION OF THE DRAWINGS

The foregoing aspects and many of the attendant advantages of this disclosed subject matter will become more readily appreciated by reference to the following detailed description, when taken in conjunction with the accompanying drawings, wherein.

DETAILED DESCRIPTION

The detailed description set forth below in connection with the appended drawings in which like numerals reference like elements is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

The following discussion relates generally to instruments suitable for use in various medical procedures of the eye. In particular, the following discussion provides examples of lenses that can be used during treatment of, for example, glaucoma.

In the following description, numerous specific details are set forth in order to provide a thorough understanding of one or more embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

Figure 1:
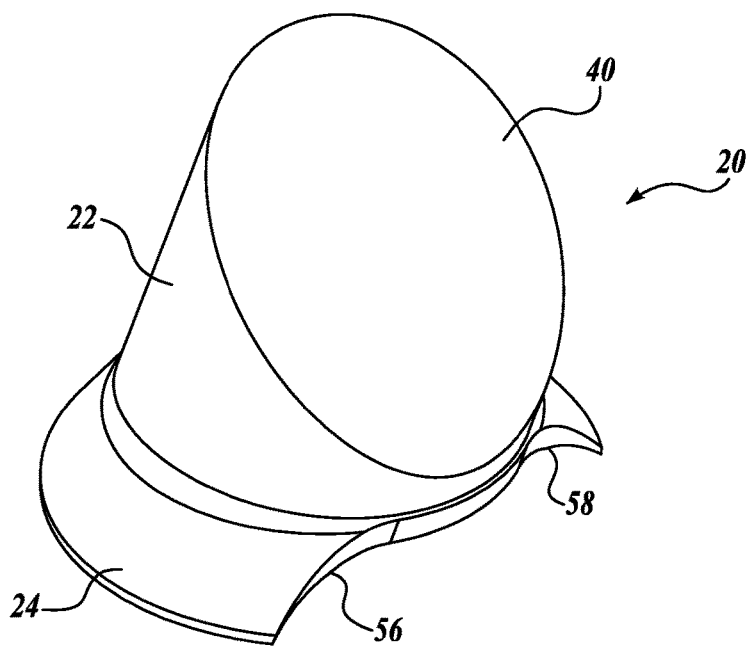
FIG. 1 is a top isometric view of a contact lens in accordance with one embodiment of the present disclosure.
Figure 2:
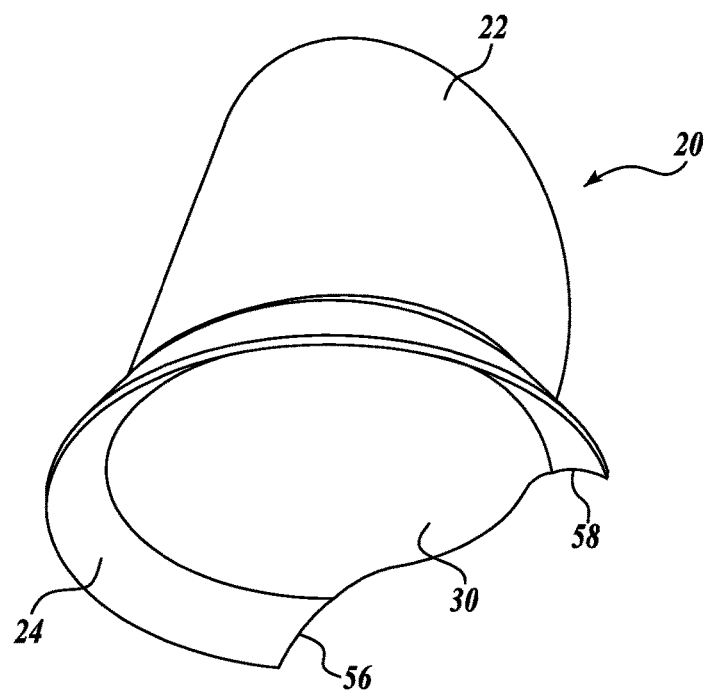
FIG. 2 is a bottom isometric view of the contact lens of FIG. 1.
Figure 3:
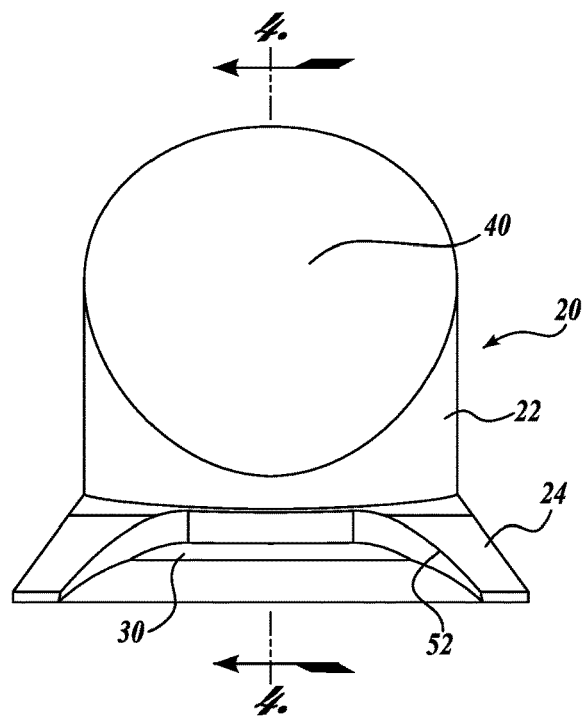
FIG. 3 is a front view of the contact lens of FIG. 1.
Figure 4:
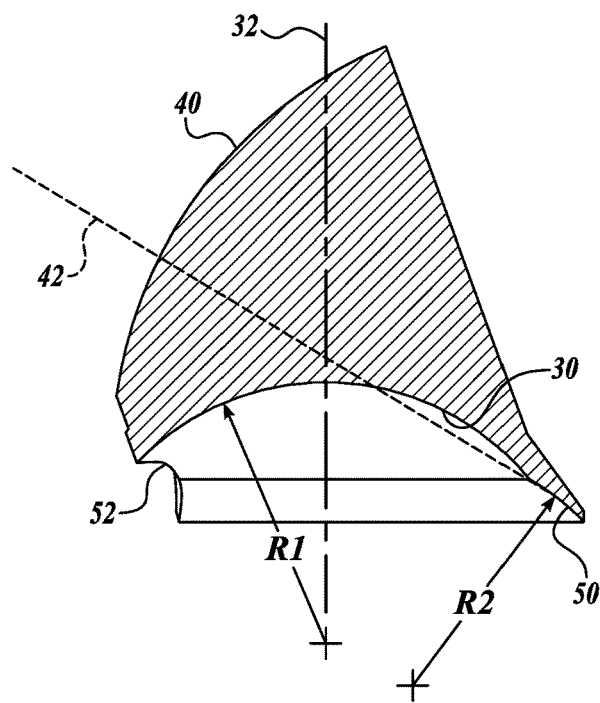
FIG. 4 is a side cross-sectional view of the contact lens of FIG. 1 taken along the lines 4-4 in FIG. 3.
Figure 5:
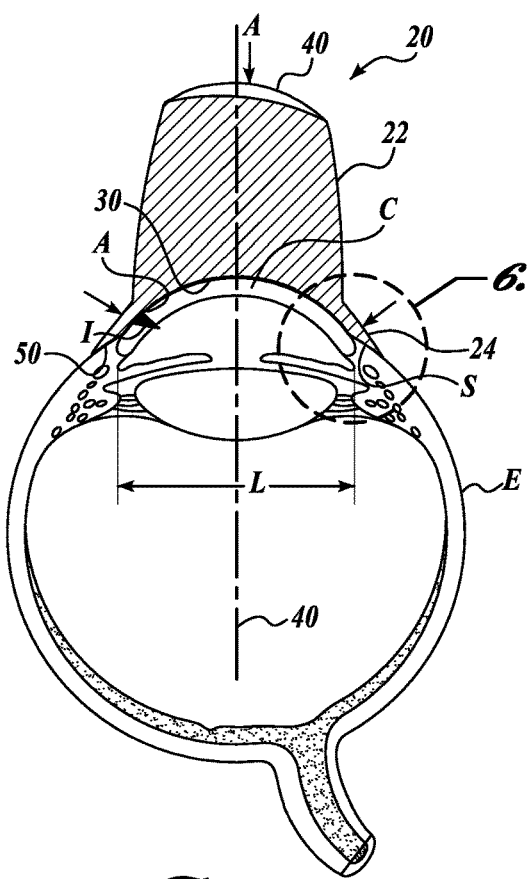
FIG. 5 is a side cross-sectional view of the contact lens of FIG. 1 when adhered to an eye.
Figure 6:
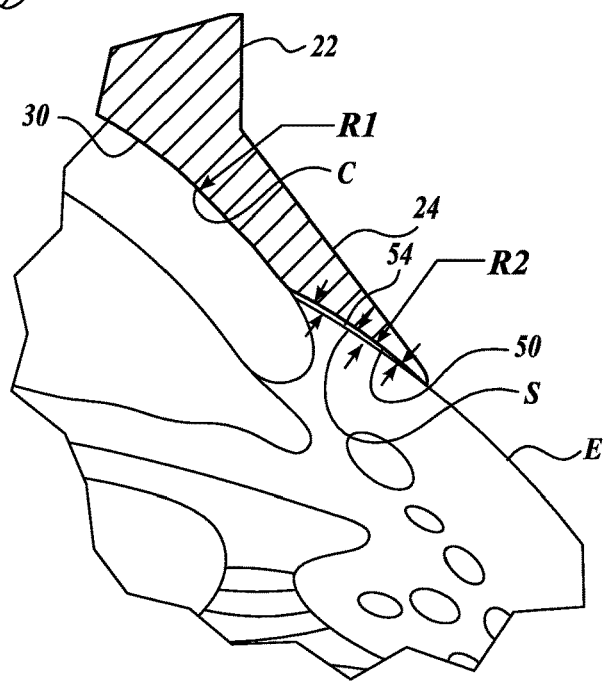
FIG. 6 is a close-up view of a portion of the side cross-sectional view of FIG. 5.
Figure 7:
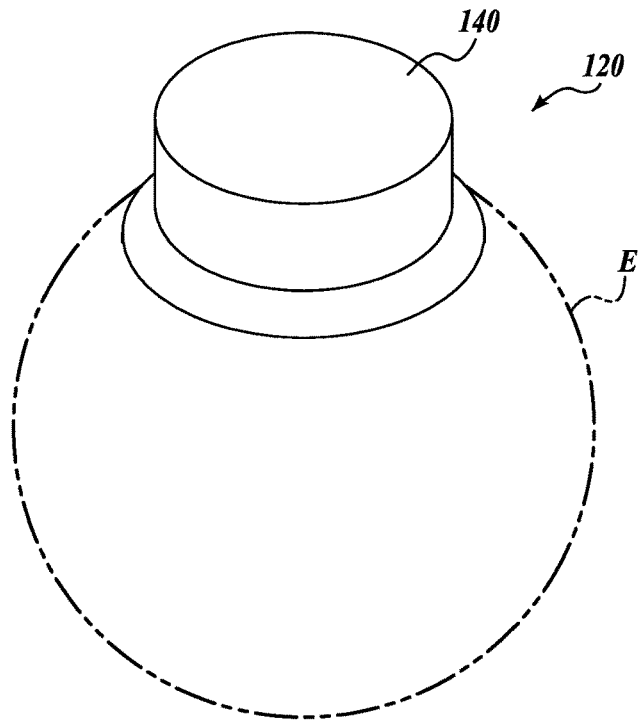
FIG. 7 is a top isometric view of a contact lens in accordance with another embodiment of the present disclosure.
Figure 8:
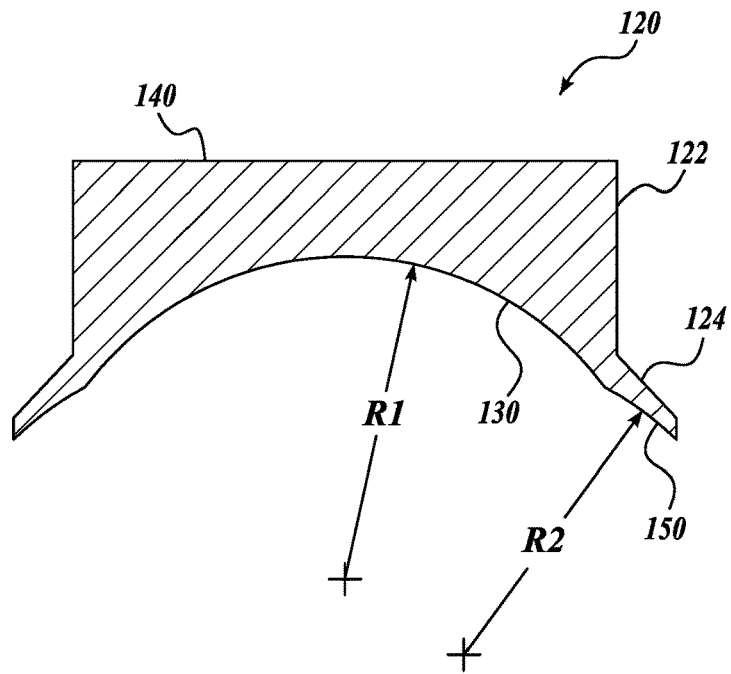
FIG. 8 is a side cross-sectional view of the contact lens of FIG. 7.
Figure 9:
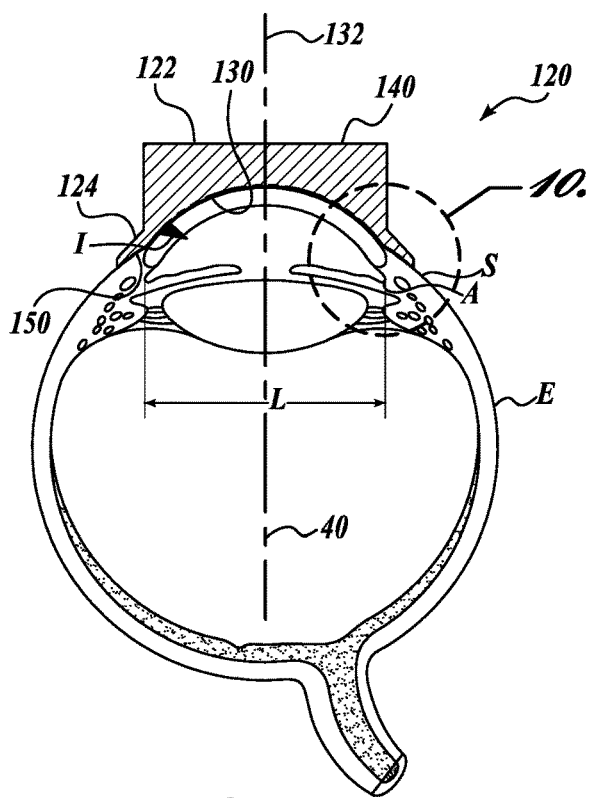
FIG. 9 is a side cross-sectional view of the contact lens of FIG. 7 in contact with an eye.
Figure 10:
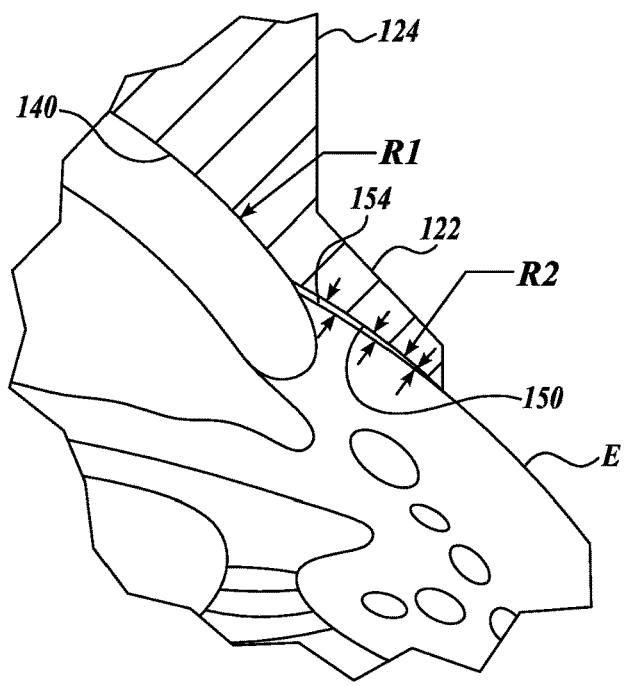
FIG. 10 is a close-up view of a portion of the side cross-sectional view of FIG. 9.
Figure 11:
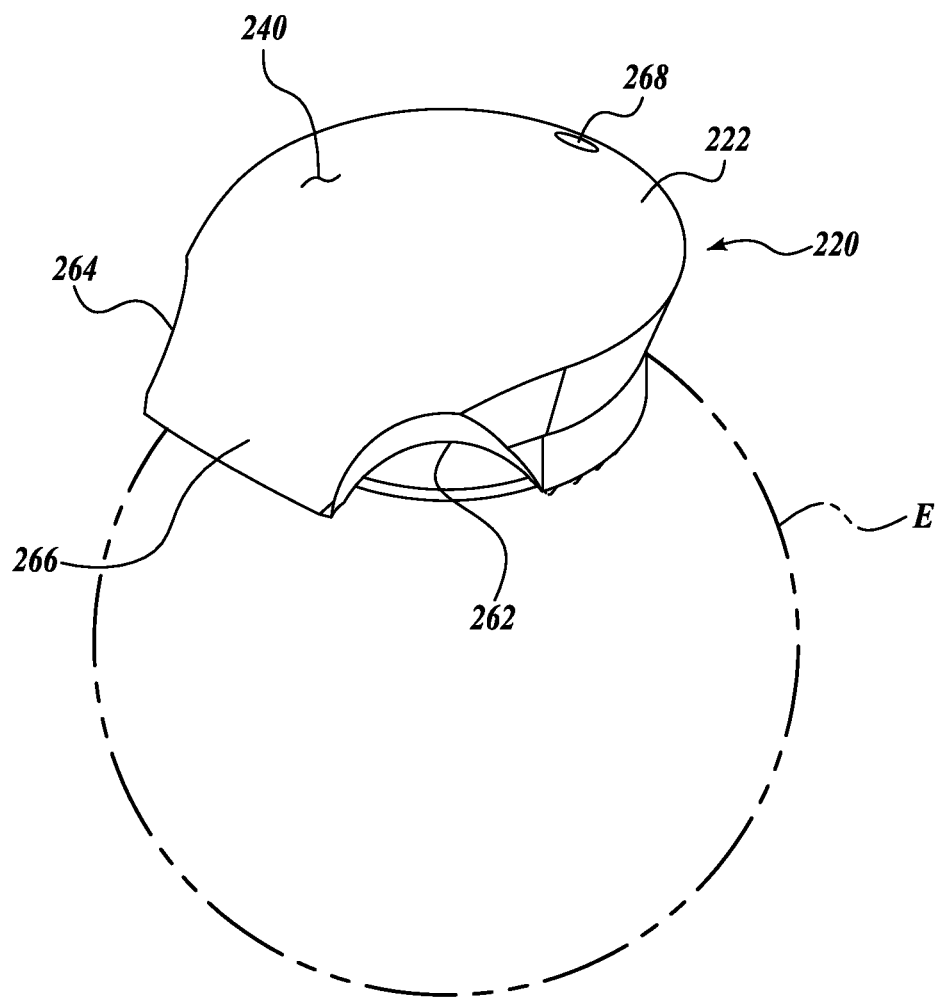
FIGS. 11-15 are views of a contact lens in accordance with another embodiment of the present disclosure.
Figure 12:
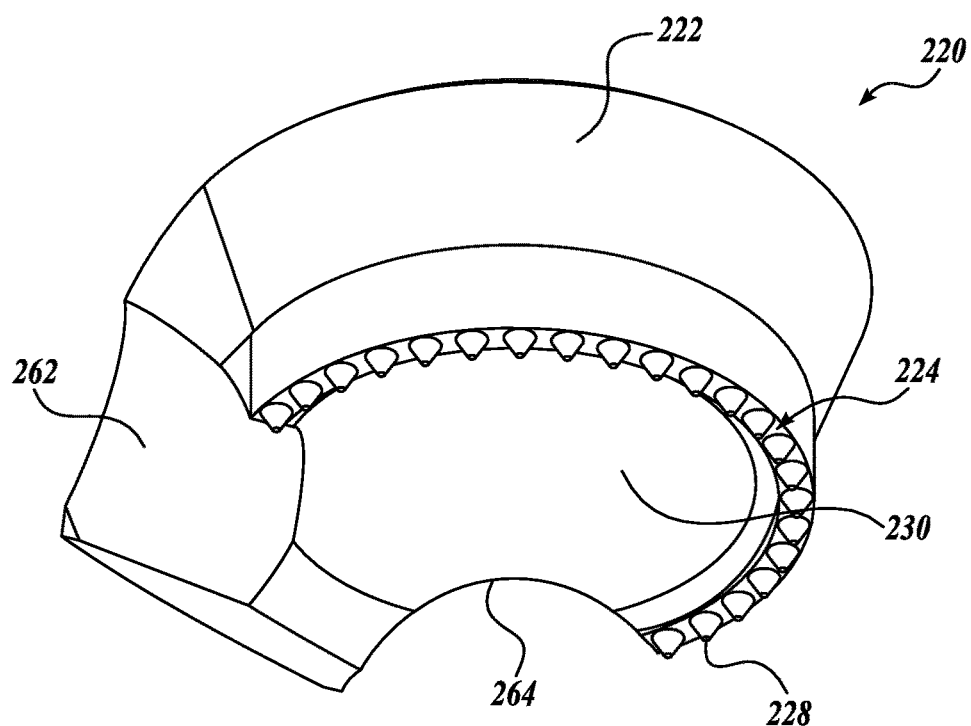
Figure 13:
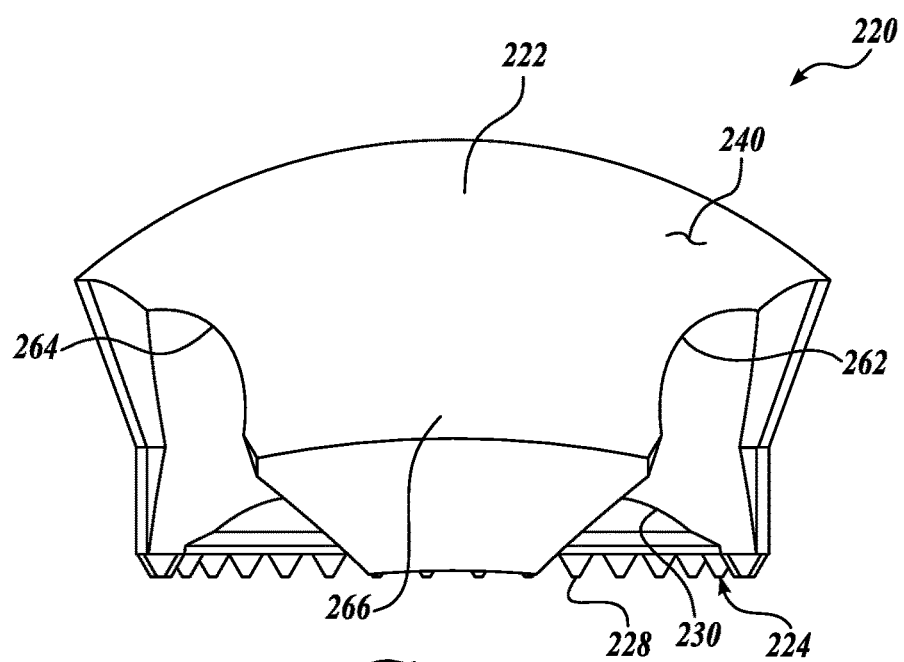
Figure 14:
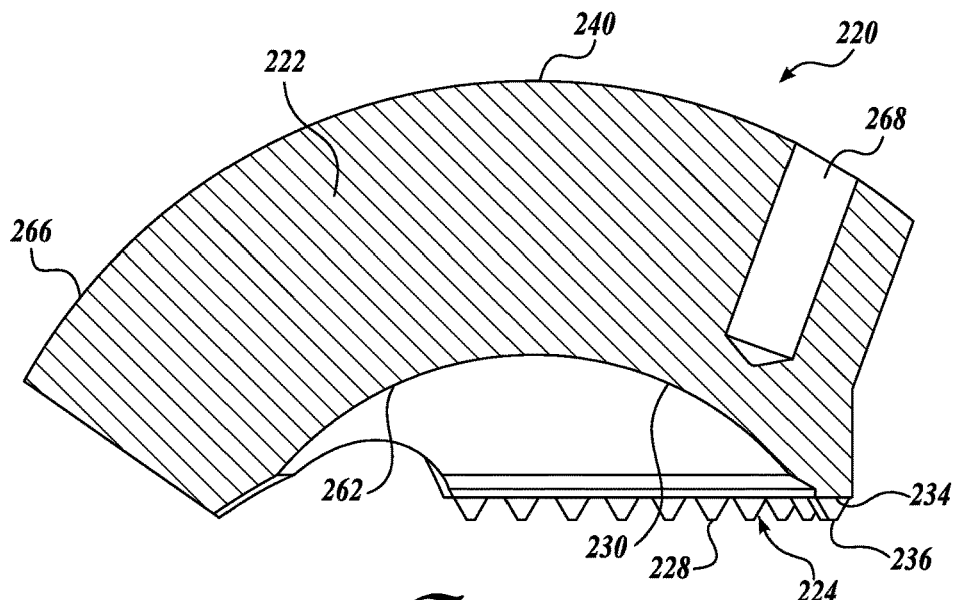
Figure 15:
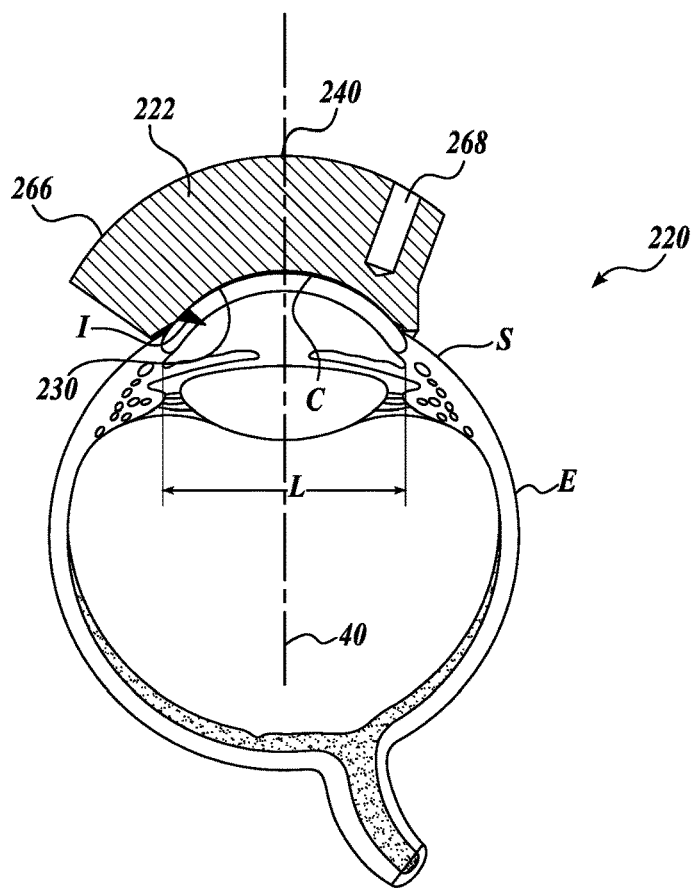

Embodiments of the present disclosure are directed to contact lenses for use in ophthalmology procedures. Referring to FIGS. 1-6, a contact lens 20 in accordance with one embodiment of the present disclosure is a flexible lens designed for direct contact and adherence to the cornea and scleral regions of an eye. Embodiments of the contact lens 20 described herein are suitable for use with a human eye, wherein the radius of curvature of the sclera is greater than the radius of curvature of the cornea. As can be seen in FIGS. 5 and 6, lens 20 is shown in contact with the cornea and sclera regions of an eye E. The lens 20 is a prism lens designed to view the periphery of the anterior chamber A of the eye E.

A common lens for use in gonioscopy (i.e., viewing of the anterior chamber of the eye) is known as the Swan-Jacob Gonioprism (the "Swan") lens. The Swan lens includes a contact lens having a contact surface that conforms to the surface of an eye. The contact surface is curved and has an optical axis that may be aligned with the optical axis of the eye. The contact lens also has a viewing surface for a user that is offset from the contact surface and has an optical axis that intersects the optical axis of the contact surface. When the contact lens is positioned on the eye, the user may view the anterior chamber of the eye by looking into the viewing surface of the lens. The contact surface may be designed so that the lens can be moved around on the cornea to view various parts of the anterior chamber.

Although the embodiment of FIGS. 1-6 is shown and described as a "Swan"-type lens, it should be appreciated that embodiments of the present disclosure may be directed to other types of lenses, for example, vitrectomy lenses (see alternate embodiment in FIGS. 7-10).

Embodiments of the present disclosure are directed to flexible lenses. Such flexible lenses may be manufactured from optically clear silicone or other flexible materials suitable as ophthalmic contact lenses. The advantage of a one-piece molded silicone contact lens is that it can be molded in one piece, the silicone is clear and provides optometric lens properties, can be sterilized, and can be disposable. However, it should be appreciated that this design may be used in a two-piece type lens. One example of a two-piece type lens may include a configuration with one piece that is flexible and contacts the eye, and one piece that is not flexible and provides a frame for a doctor to suture or otherwise secure the frame to the patient's face.

Referring to FIGS. 1-6, lens 20 includes a central lens portion 22 and an annular eye fixation portion 24 extending radially outwardly from the outer periphery of the posterior end (or contact end) of the central lens portion 22. The central lens portion 22 may be sized to cover the entire cornea C of the eye E, with the eye fixation portion 24 providing additional surface area to aid in contact of the lens 20 to the sclera S of the eye E.

The diameter of an average cornea is about 12 mm. In one embodiment of the present disclosure, the central lens portion 22 may be sized to be smaller than the size of the average cornea. In one embodiment of the present disclosure, the lens 20 may be sized to have a diameter of the posterior surface 30 of the central lens portion 22 to be in the range of 10 to about 12 mm. In one embodiment of the present disclosure, the lens 20 may be sized to have a diameter of the posterior surface 30 of the central lens portion 22 to be in the range of about 11.0 mm to about 11.4 mm. In one embodiment of the present disclosure, the lens 20 may be sized to have a diameter of the posterior surface 30 of the central lens portion 22 to be about 11.2 mm.

In one embodiment of the present disclosure, the lens 20 may be sized to have an outer diameter on the eye fixation portion 24 to be in the range of 14 to about 16 mm. In one embodiment of the present disclosure, the lens 20 may be sized to have an outer diameter on the eye fixation portion 24 to be in the range of about 14.8 mm to about 15.2 mm. In one embodiment of the present disclosure, the lens 20 may be sized to have an outer diameter on the eye fixation portion 24 to be about 15 mm.

In the illustrated embodiment, the posterior surface 30 of the central lens portion 22 is concave in shape and conforms to and is compatible with the convex anterior surface of an eye E (see FIGS. 5 and 6). In that regard, the posterior surface 30 is designed and configured for contacting the eye E. In the illustrated embodiment of FIGS. 1-6, the posterior surface has an optical axis 32 (see FIG. 4).

The central lens portion 22 also includes an anterior surface 40 that is positioned anterior to the contact lens surface 30 and is a viewing surface. The anterior surface 40 may be curved and has an optical axis 42. To view the periphery of the anterior chamber A of the eye E using the contact lens 20, the viewer views in a general direction along the optical axis 42 of the anterior surface 40 of the contact lens 20.

The eye fixation portion 24 extends from the outer perimeter of the central lens portion 22 and, for example, provides additional surface area for adherence of the contact lens 20 to the eye E. The eye fixation portion 24 is flexible in nature, and because of its thickness may flex when pressed against an eye E. In one embodiment of the present disclosure, the thickness of the eye fixation portion may be in the range of about 0.25 mm to about 0.50 mm. In one embodiment of the present disclosure, the thickness of the eye fixation portion may be about 0.40 mm.

In the illustrated embodiment, a portion of the posterior surface of the eye fixation portion 24 conforms and has a similar radius of curvature as the posterior surface 30 of the central lens portion 22. However, the outer annular end of the eye fixation portion 24 has annular posterior surface 50 having a different radius of curvature than the posterior surface 30 of the central lens portion 22.

In accordance with embodiments of the present disclosure, the posterior surface 50 of the eye fixation portion 24 has a different radius of curvature than the posterior surface 30 of central lens portion 22. In the illustrated embodiment, the posterior surface 30 of the central lens portion 22 has a radius of curvature R1 that approximates the radius of curvature of the cornea C. The posterior surface 50 of the eye fixation portion 24 attached to the central lens portion has a radius of curvature R2 that is less than R1 and is less than the radius of curvature of the sclera. In one embodiment of the present disclosure, the ratio between R2 and R1 may be in the range of about 1 to 1.05 to 1 to 1.15. In one embodiment of the present disclosure, the ratio between R2 and R1 is 1 to 1.10.

A previously designed lens uses another physical principle for adhering to an eye. For example, U.S. Pat. Nos. 6,120,147 and 6,412,946 are directed to silicone ophthalmic contact lenses primarily designed for use during vitrectomy surgery. The outer flange includes an annular interior concave surface joined to the interior concave surface of the central lens portion. The interior concave surface has a radius of curvature R2 that is larger than the radius of curvature of the cornea and radius R1, but smaller than the radius of curvature of the average sclera. By providing the interior concave surface with a radius of curvature R2 that is smaller than the radius of curvature of the average sclera, the previously designed lens deforms to match the shape of the sclera and provide capillary traction for adherence of the lens to the eye.

In contrast to these previous designs, embodiments of the present disclosure have an eye fixation portion 24 (or outer flange) having a radius of curvature R2 that is smaller than the radius of curvature of the cornea and radius R1. The radius of curvature R2 is also smaller than the radius of curvature of the average sclera. In addition, the axis from which R2 is measured is offset from center to provide improved contact with the sclera. In that regard, the inventors have found that an offset radius of curvature provides a posterior surface 50 of the eye fixation portion 24 having improved contact with the sclera.

Although not wishing to be bound by theory, it is believed by the inventors that the effect of the R2-R1 relationship is that, rather than the flange contacting the sclera using capillary traction as in the previously designed lens, a pocket 54 is formed between the eye fixation portion 24 and the sclera S forming a vacuum for a suction effect (see FIG. 6). The pocket 54 may be filled with topical fluids from the eye or other added fluids used during the procedure. These fluids may aid in creating a vacuum and also may provide lubrication to aid in the user moving the contact lens on the patient's eye as needed. Such movement may be useful in a glaucoma surgical procedure, but is not necessary in a vitrectomy procedure. Therefore, the pocket 54 allows the lens 20 to move, while the capillary traction effects of the previously designed lens prevent such ease of motion.

In the illustrated embodiment of FIGS. 1-6, the lens 20 optionally includes a cut-out portion 52 only in the outer perimeter of the eye fixation portion 24 which may be used for surgical access. The cut-out portion 52 is configured such that the eye fixation portion 24 only covers a portion of the annular perimeter of the contact lens 20 and not the entire perimeter. The cut-out portion 52 may also extend into the central lens portion 22 and is designed and configured to receive surgical instruments to allow access to the cornea for surgical procedures, for example, during glaucoma surgery procedures. The cut-out portion 52 allows access to the cornea for use of a surgical instrument to make a surgical incision in the cornea and scleral regions of the eye and/or insert a stent in the eye.

One advantage of using a flexible lens in surgical procedures is that doctors are able to use instruments on the eye in conjunction with the lens. If the lens is not flexible and rather is rigid, the lens may tend to "decouple" or separate from the cornea as the cornea changes shape when a surgical instruments is inserted. It is difficult to see into the eye if the lens decouples from the cornea. In that regard, any slight decoupling or separation of the lens from the cornea creates a reflective area that make the view of the anterior chamber angle difficult for the user. The inventors have found that flexible lenses in accordance with embodiments of the present disclosure do not tend to decouple from the cornea as the cornea changes shape, and rather, continue to remain attached to the cornea.

It should be appreciated that lenses with continuous outer flanges and without cut-out portions are also within the scope of the present disclosure. See, for example, an alternative embodiment shown in FIGS. 7-10.

Returning to the illustrated embodiment, the cut-out portion 52 has a contoured shape along the outer perimeter of the central lens portion 22. The cut-out portion may extend around between 20% and 40% of the outer circumference of the eye fixation portion 24. The lens 20 is designed and configured to be able to suitably adhere to the eye E, even though it includes a cut-out portion 52. In that regard, the shape of the cut-out portion 52 provides vacuum force along the remaining eye fixation portion 24 and at the ends 56 and 58 where the eye fixation portion 24 is truncated (see FIGS. 1 and 2). Therefore, the contoured design of the cut-out portion 52 helps to maintain the vacuum force in the pocket 54 by allowing the truncated ends 56 and 58 of the eye fixation portion 24 to form a seal with the eye.

In use, referring to FIGS. 5 and 6, the lens 20 is placed upon the eye E of a patient and pressed against the eye in the direction of arrow A. Because R2 is less than R1, it is believed by the inventors that the eye fixation portion 24 forms a "cup" against the eye E in order to form a pocket. In other embodiments of the present disclosure, R2 may be equal to R1 or R2 may be greater than R1.

The illustrated embodiment of FIGS. 1-6 may be useful in glaucoma examination and/or surgical procedures, such as for example, open or wide-angle glaucoma procedures as will be described in greater detail below. Generally described, aqueous humor, a fluid produced within the eye, drains via the trabecular meshwork into the canal of Schlemm, then into the scleral plexuses. The major risk factor for most glaucomas, and the focus of treatment, is relieving increased intraocular pressure, which is a function of the production of liquid aqueous humor without adequate drainage. In open/wide-angle glaucoma, flow is reduced through the trabecular meshwork as a result of degeneration and/or obstruction of the trabecular meshwork. To relieve the increased intraocular pressure, one or more stents may be inserted into the trabecular meshwork.

To insert such stents during an open-angle glaucoma surgical procedure, the user may move the lens 20 to a first position on the eye E to perform a procedure, for example, to insert or implant a first stent into the anterior chamber A of the eye E through the cut-out portion 52 of the lens 20, then to a second position on the eye E to perform a procedure, for example, to insert or implant a second stent into another place in the anterior chamber A of the eye E through the cut-out portion 52 of the lens 20. The rotation of the lens 20 for stent implantation is about the axis of the patient's eye.

Likewise, during an examination procedure, the user may move the lens 20 from a first position on the eye E to examine a first portion of the anterior chamber A, then to a second position on the eye E to examine a second portion of the anterior chamber A. It should further be appreciated that embodiments of the present disclosure may also be used in closed-angle glaucoma surgical procedures.

Referring now to FIGS. 7-10, another embodiment of the present disclosure will be described. The lens 120 of FIGS. 7-10 is substantially similar to the lens 20 of FIG. 1-6, except for differences regarding the central lens portions 122 and the eye fixation portion 124. Like elements in the lens 120 of FIGS. 7-10 use like numerals as in the lens 20 in FIGS. 1-6, except enumerated in the 100 series.

The contact lens 120 shown in the illustrated embodiment of FIGS. 7-10 may be useful in vitrectomy examination and/or surgical procedures. In a vitrectomy procedure, surgical tools are inserted into the eye E away from the cornea into the vitreous body of the eye E, behind the lens of the eye E. Because the surgical incision is away from the contact lens 120, a cut-out portion is not needed in the contact lens 120. Therefore, the eye fixation portion 124 of the contact lens 120 is a continuous annular portion without a cut-out portion.

The contact lens 120 of the illustrated embodiment further includes an anterior surface 140 that is a direct viewing lens for the user to view into the patient's eye along the optical viewing axis 132. However, it should be appreciated that angled viewing portions (for example, like anterior surface 40 in the embodiment shown in FIGS. 1-6) are also within the scope of the present disclosure.

In the illustrated embodiment of FIGS. 7-10, the radius of curvature R2 is smaller than the radius of curvature of the cornea and radius R1. The radius of curvature R2 is also smaller than the radius of curvature of the average sclera. In addition, the axis from which R2 is measured is offset from center to provide improved contact with the sclera. In another embodiment of the present disclosure, the radius of curvature R2 is equal to the radius of curvature of the cornea and radius R1.

Referring now to FIGS. 11-21, other embodiments of the present disclosure will be described. The respective lenses 220, 320, 420, and 520 of FIGS. 11-21 are substantially similar to the lenses 20 and 120 of FIG. 1-10, except for differences regarding the central lens portions and the eye fixation flange. Like elements in the lenses of FIGS. 11-21 use like numerals as the lens 20 in FIGS. 1-6, except enumerated in the 200, 300, 400, and 500.

Referring to FIGS. 11-15, a lens 220 in accordance with another embodiment of the present disclosure is provided. The lens 220 includes a central lens 222 having a contact (posterior) surface 230 and a viewing (anterior) surface 240. The contact surface 230 has a radius of curvature that approximates the radius of curvature of the cornea. An eye fixation system 224 is attached to the central lens 222. The eye fixation system 224 includes a plurality of protrusions 228 extending from or near at least a portion of the perimeter of the central lens 222. Each protrusion 228 is configured to interface with the sclera, and each protrusion has a first end 234 and a second end 236, the first end 234 being attached to the central lens 222 and the second end 236 extending away from the central lens 222 (see FIG. 14).

In the illustrated embodiment, the protrusions 228 extend around at a portion of the perimeter of the contact surface 230 of the central lens. However, in other embodiments, the protrusions may extend around the entire perimeter of the contact surface of the central lens. In the illustrated embodiment, the second end 236 of each of the plurality of protrusions 228 is flat. However, the second end may also be rounded (see, for example, the embodiment of FIGS. 18 and 19). In addition, the lens 220 may include any number of protrusions to achieve adequate contact with the patient's eye (compare FIGS. 18 and 19).

The lens 220 includes two cut-out portions 262 and 264 designed and configured to receive surgical instruments to allow access to the cornea for surgical procedures, for example, during glaucoma surgery procedures. Although showing two cut-out portions 262 and 264 in the illustrated embodiment to enable both left-handed and right-handed approaches, a lens having one cut-out portion is also within the scope of the present disclosure (see, for example, FIGS. 16 and 17).

In the illustrated embodiment of FIGS. 11-15, the viewing surface 240 includes an extended section 266 to enhance the visualization into the lens 220 for the doctor.

In the illustrated embodiment, the lens 220 further includes a hole 268 extending from the viewing surface 240 into the body of the central lens 222. The hole 260 is adapted to accept a tool or handle for manipulation of the contact lens 220 on the patient's eye. In the illustrated embodiment, the hole is a blind hole to prevent the tool from mistakenly engaging the patient's eye.

Figure 16:
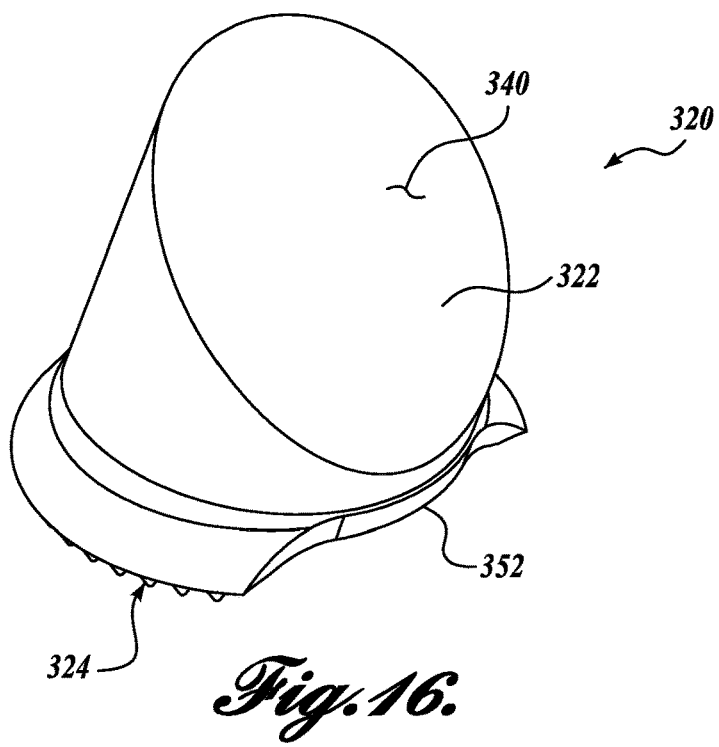
FIGS. 16 and 17 are views of a contact lens in accordance with another embodiment of the present disclosure.
Figure 17:
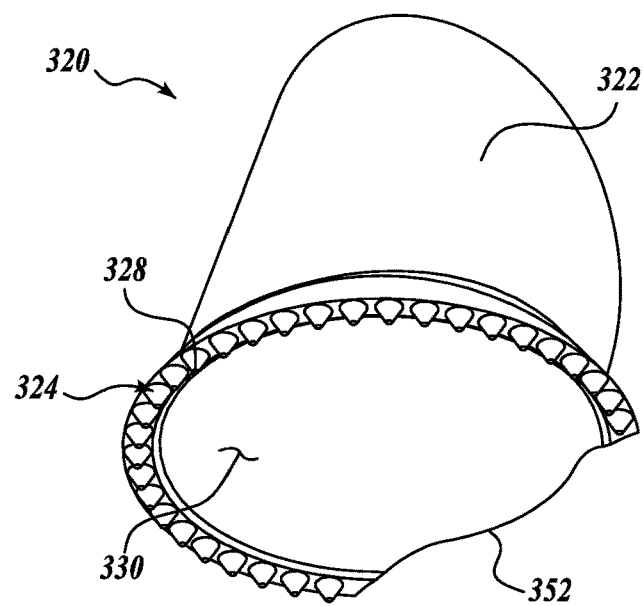

Now referring to FIGS. 16 and 17, a lens 320 in accordance with another embodiment of the present disclosure is provided. The lens 320 includes a central lens 322 having a contact (posterior) surface 330 and a viewing (anterior) surface 340. Like the lens 220 of FIGS. 11-15, the lens 320 of FIGS. 16 and 17 includes an eye fixation system 324 attached to the central lens 322. The eye fixation system 324 includes a plurality of protrusions 328 extending from or near at least a portion of the perimeter of the central lens 322. Like the lens 220 of FIGS. 11-15, the lens 320 of FIGS. 16 and 17 includes one cut-out portion 352 and does not include an extended section of the viewing surface 340.

Figure 18:
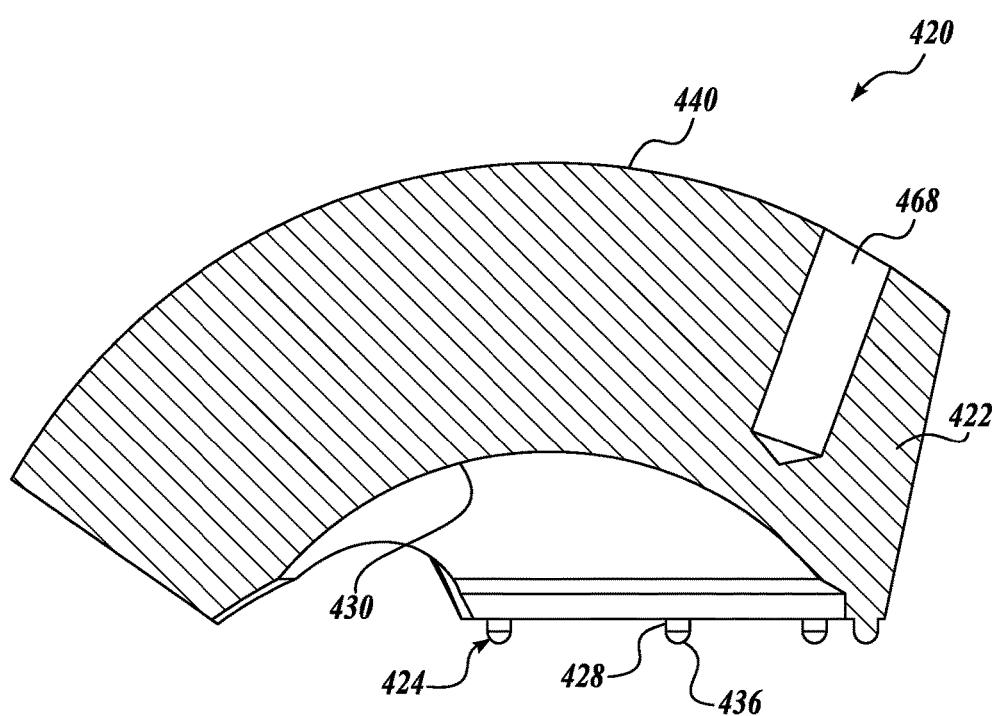
FIGS. 18 and 19 are views of a contact lens in accordance with another embodiment of the present disclosure.
Figure 19:
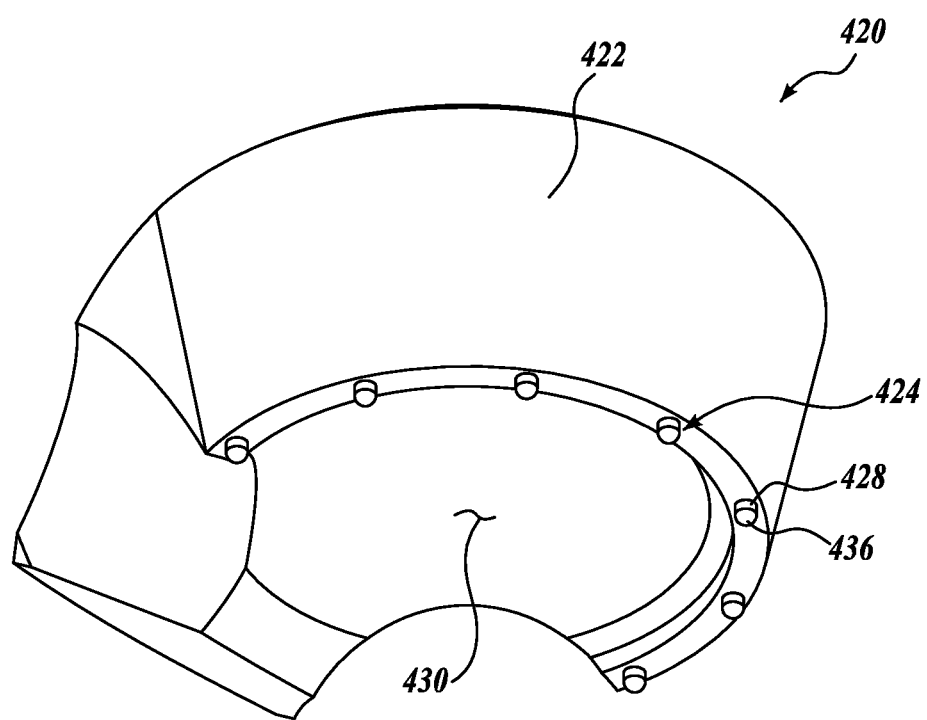

Now referring to FIGS. 18 and 19, a lens 420 in accordance with another embodiment of the present disclosure is provided. The lens 420 includes a central lens 422 having a contact (posterior) surface 430 and a viewing (anterior) surface 440 and is similar to the lens 220 of FIGS. 11-15. The lens 420 of FIGS. 18 and 19 includes an eye fixation system 424 including a plurality of protrusions 428 extending from the central lens 422 for contact with the patient's eye, wherein second end 436 of each of the plurality of protrusions 428 is rounded.

Figure 20:
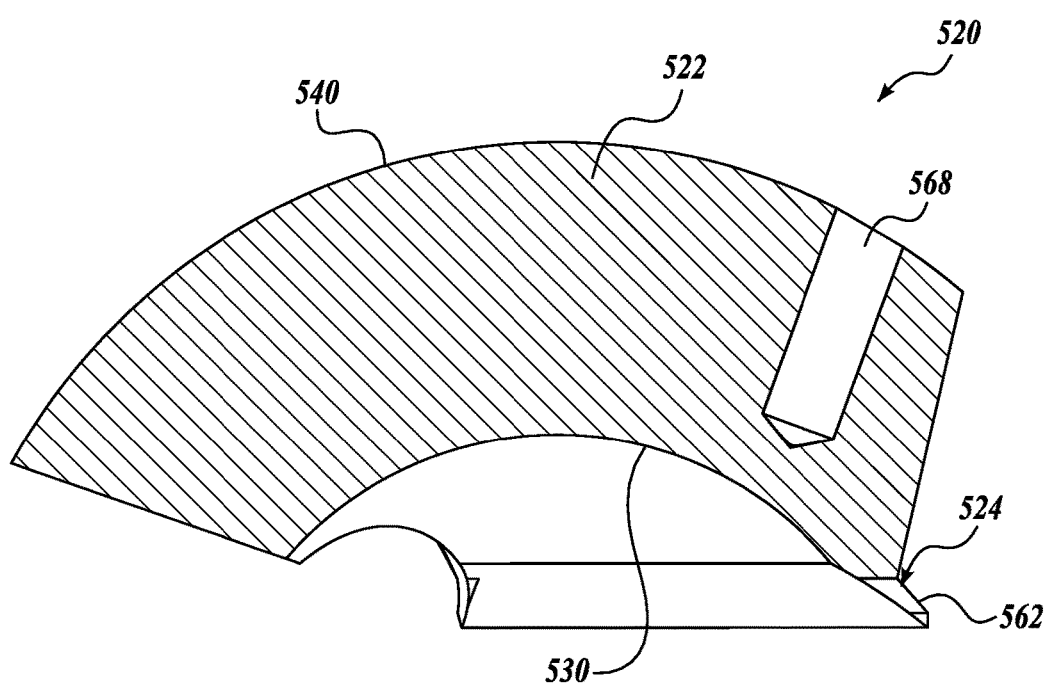
FIGS. 20 and 21 are views of a contact lens in accordance with another embodiment of the present disclosure.
Figure 21:
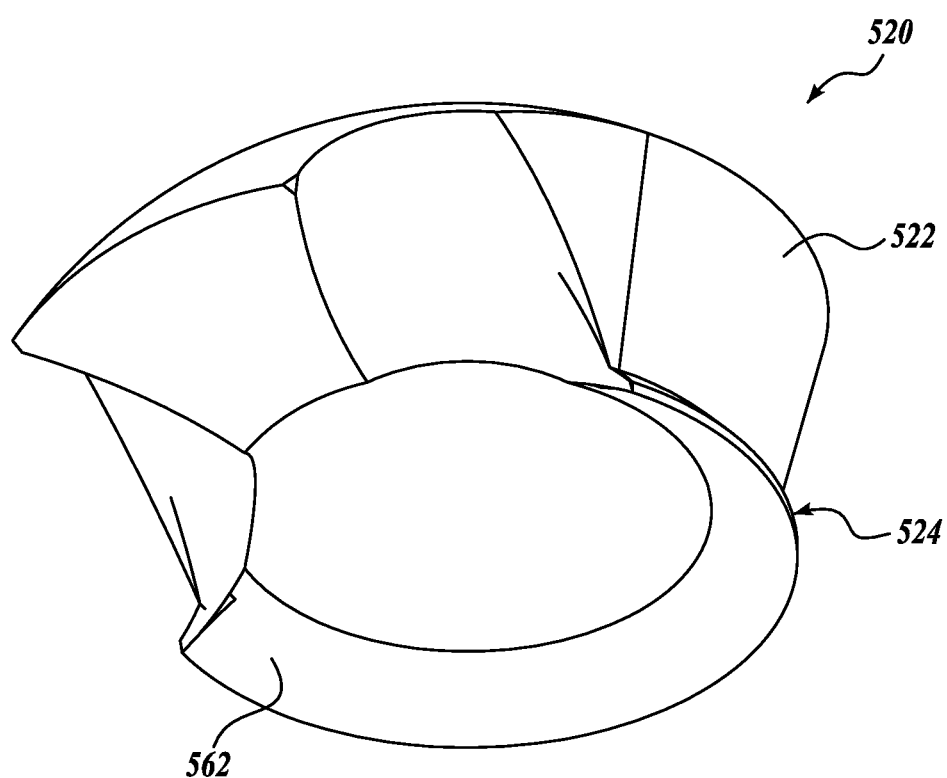

Now referring to FIGS. 20 and 21, a lens 520 in accordance with another embodiment of the present disclosure is provided. The lens 520 includes a central lens 522 having a contact (posterior) surface 530 and a viewing (anterior) surface 540 and is similar to the lens 220 of FIGS. 11-15. The lens 520 of FIGS. 18 and 19 includes an eye fixation system 524 including a continuous flange portion 562 extending from the central lens 422 for contact with the patient's eye. Like the other embodiments described above, the eye fixation system may have an R1/R2 relationship with R2 less than R1, R2 equal to R1, or R2 greater than R1.

While illustrative embodiments have been illustrated and described, it will be appreciated that various changes can be made therein without departing from the spirit and scope of the disclosure.

The embodiments of the invention in which an exclusive property or privilege is claimed are defined as follows:

1. A self-adhering, flexible gonioscopic lens for adhering to cornea and scleral regions of an eye, the gonioscopic lens comprising:

a body, which is a single piece of silicone, the body including a central lens portion including a contact surface and a viewing surface, the contact surface having a radius of curvature that approximates the radius of curvature of the cornea and an eye fixation system configured for fixing the central lens to the eye, wherein the eye fixation system is extends from the perimeter of the contact surface of the central lens extending around only a portion of the perimeter of the contact surface of the central lens to define a cut-out portion in the eye fixation system of the gonioscopic lens, wherein the eye fixation system includes a flange portion extending from a first radius where the eye fixation system is attached to the perimeter of the contact surface to a second radius larger than the first radius, and wherein the eye fixation system allows for the gonioscopic lens to self-adhere to an eye and remain in position without support.

2. The gonioscopic lens of claim 1, wherein the cut-out portion is shaped such that at least one surgical tool can access the cornea region of the eye without moving the gonioscopic lens.

3. The gonioscopic lens of claim 1, wherein the viewing surface is flat.

4. The gonioscopic lens of claim 1, wherein the viewing surface is prismatic.

5. The gonioscopic lens of claim 1, wherein the viewing surface is rounded.

6. The gonioscopic lens of claim 1, wherein the central lens includes at least one hole extending from the viewing surface into the body of the central lens, the at least one hole adapted to accept a tool for moving the gonioscopic lens.

7. The gonioscopic lens of claim 6, wherein the at least one hole is a blind hole.

8. The gonioscopic lens of claim 1, wherein the gonioscopic lens is configured for movement on the eye of the patient.

9. A self-adhering, flexible gonioscopic lens configured for adhering to cornea and scleral regions of an eye of a patient, the gonioscopic lens comprising:

(a) a central lens having a body including a contact surface and a viewing surface;

(b) an eye fixation system extending around a portion of the perimeter of the contact surface of the central lens, the eye fixation system defining a cut-out portion through the eye fixation system configured for providing access for a surgical instrument to the cornea region of the eye when the gonioscopic lens is adhered to the eye of the patient, wherein the gonioscopic lens is a single piece of silicone, wherein the eye fixation system includes a flange portion extending from a first radius where the eye fixation system is attached to the perimeter of the contact surface to a second radius larger than the first radius, and wherein the eye fixation system allows for the gonioscopic lens to self-adhere to an eye and remain in position without support.

* * * * *

UNITED STATES PATENT AND TRADEMARK OFFICE
CERTIFICATE OF CORRECTION

PATENT NO. : 10,413,178 B2  
APPLICATION NO. : 15/457745  
DATED : September 17, 2019  
INVENTOR(S) : R. D. Graham et al.

Page 1 of 1

It is certified that error appears in the above-identified patent and that said Letters Patent is hereby corrected as shown below:

| Column | Line | Error |
|---|---|---|
| 10 (Claim 1, Line 10) | 7 | "system is extends" should read --system extends-- |

Signed and Sealed this  
Seventh Day of April, 2020

Andrei Iancu  
*Director of the United States Patent and Trademark Office*